United States Patent

Pfahl et al.

[11] Patent Number: 6,004,748
[45] Date of Patent: Dec. 21, 1999

[54] METHOD OF INHIBITING TRANSCRIPTION UTILIZING NUCLEAR RECEPTORS

[75] Inventors: Magnus Pfahl, Solana Beach; Michael Karin, San Diego, both of Calif.

[73] Assignee: La Jolla Cancer Research Foundation, La Jolla, Calif.

[21] Appl. No.: 08/757,349

[22] Filed: Nov. 27, 1996

Related U.S. Application Data

[63] Continuation of application No. 08/182,735, Jan. 14, 1994, Pat. No. 5,643,720, which is a continuation of application No. 08/032,726, Mar. 16, 1993, abandoned, which is a continuation of application No. 07/595,582, Oct. 10, 1990, abandoned.

[51] Int. Cl.$^6$ .......................... C12Q 1/68; C07K 14/705; C07H 21/04
[52] U.S. Cl. .................. 435/6; 530/358; 530/359; 536/23.1; 536/24.1
[58] Field of Search .................. 435/6; 530/358, 530/399; 536/23.1, 24.1

[56] References Cited

U.S. PATENT DOCUMENTS 5,639,592 6/1997 Evans et al. .................. 435/4

FOREIGN PATENT DOCUMENTS 0 552 202B1 1/1996 European Pat. Off. ....... G01N 33/74
WO 92/05447 4/1992 WIPO ............... G01N 33/74

OTHER PUBLICATIONS

Jonat et. al.. (B) Positive and negative reglation of collagenase gene expression. Proceedings of the Metalloproteinase Conference. Destin, Florida. pp. 145–155. H. birkedal–Hansen, Z. Werb, H. Welgus, and H. van Wart eds., Sep. 1989.

Glass et. al.. Positive and Negative regulation of gene trascription by a retinoic acid–thyroid hormoe receptor heterodimer. Cell. vol.. 59:697–708, Nov. 17, 1989.

Mangelsdorf et. al.. Nuclear receptor that identifies a novel retinoic acid response pathway. Nature. vol.. 345:224–229, May 17, 1990.

Krust et. al.. a third human retinoic acid receptor, hRAR–gamma. PNAS (USA). vol.. 86:5310–5314, Jul. 1989.

Evans, R. The steroid and thyroid hormone receptor superfamily. Science. vol.. 240:889–895, May 13, 1988.

Mordacq and Linzer, "Co–localization of Elements Required for Phorbol Ester Stimulation and Glucocorticoid Repression of Proliferin Gene Expression," *Genes Dev.* 3:760–769 (1989).

Muller et al., "The Collagenase Gene Family in Humans Consists of at Least Four Members," *Biochem. J.* 253:187–192 (1988).

Offringa et al., "Similar Effects of Adenovirus E1A and Glucocorticoid Hormones on the Expression of the Metalloprotease Stromelysin," *Nucl. Acids Res.* 16:10973–10983 (1988).

Schüle et al., "Functional Antagonism between Oncoprotein c–Jun and the Glucocorticoid Receptor," *Cell* 62:1217–1226 (1990).

(List continued on next page.)

*Primary Examiner*—Nancy Degen
*Assistant Examiner*—Williams Sandals
*Attorney, Agent, or Firm*—Campbell & Flores LLP

[57] ABSTRACT

This invention provides a method of inhibiting the transcription of a gene, which is activated by AP-1 or an AP-1 component, comprising binding AP-1 or the component with a nuclear receptor so as to prevent the binding of AP-1 to the gene. The nuclear receptor can be the retinoic acid receptor, glucocorticoid receptor, vitamin D3 receptor, thyroid receptor, or estrogen receptor. Also provided is a composition of matter comprising AP-1 or an AP-1 component bound to a nuclear receptor. These methods and compositions can be used to treat arthritis and cancer.

22 Claims, 6 Drawing Sheets

OTHER PUBLICATIONS

Yang–Yen et al., "Transcriptional Interference between c–Jun and the Glucocorticoid Receptor: Mutual Inhibition of DNA Binding due to Direct Protein–Protein Interaction," *Cell* 62:1205–1215 (1990).

Brinckerhoff, C.E. and Harris, E.D., Modulation by retinoic acid and corticosteroids of collagenase production by rabbit synovial fibroblasts treated with phorbol myristate acetate or poly(ethylene glycol), Biochem. Biophys. Acta. (1981).

Lafyatis et al., Interleukin–1 stimulates and all–trans–retinoic acid inhibits collagenase gene expression through its 5' activator protein–1 binding site, Mol. Endo. 4:973–980 (1990).

Yang–Yen et al., Transcriptional interference between c–Jun and glucocorticoid receptor: mutual inhibition of DNA–binding due to direct protein–protein interaction, Cell 62:6:1205–1215 (1990).

Schule et al., Functional antagonism between oncoprotein c–Jun and the glucocroticoid receptor, Cell 62:1217–1226 (1990).

Jonat, C. et al., "Antitumor Promotion and Antiinflammation:Down–Modulation of AP–1 (Fos/Jun) Activity byG lucocorticoid Hormone," Cell 62:1189–1204 (1990).

Drouin et al., "Glucocorticoid receptor binding to a specific DNA sequence is required for hormone–dependent inhibition of pro–optomelanocortin gene transcription", *Mol. Cell Biol.*, 9:5305–5314 (1989).

Offringa et al., "Similar effects of adenovirus EIA and glucocorticoid hormones on the expression of the metalloprotease stromelysin," *Nucl. Acids Res.*, 16:10974–10983 (1988).

Mordacq, J.C. and Linzer, D.I.II., "Co–localization of elements required for phorbol ester stimulation and glucocorticoid repression of proliferin gene expression," *Genes Dev.*, 3:760–769 (1989).

Muller et al., "The collagenase gene family in humans consists of at least four members," *Biochem J.*, 235:187–192.

Brinckerhoff, C.E. and Harris, E.D., "Modulation by retinoic acid and corticosteroids of collagenase production by rabbit synovial fibroblasts treated with phorbol myristate acetate of poly(ethylene glycol)," *Biochem. Biophys. Acta.*, (1981).

Lafyatis et al., "Interleukin–1 stimulates and all–trans–retinoic acid inhibits collagenase gene expression through its 5' activator protein–1 binding site," *Mol. Endo.*, 4:973–980 (1990).

Yang–yen et al., Transcriptional interference between c–Jun and glucocorticoid receptor: mutual inhibition of DNA–binding due to direct protein–protein interaction, *Cell*, 62:6:1205–1215 (1990).

Schule et al., "Functional antagonism between oncoprotein c–Jun and the glucocorticoid receptor," *Cell*, 62:1217–1226 (1990).

Jonat et al., "Antitumor Promotion and Antiinflammation::Down–Modulation of AP–1 (Fos/Jun) Activity by Glucocorticoid Hormone," *Cell*, 62:1189–1204 (1990).

Lehmann, et al., "$RAR_\gamma 2$ Expression is Regulated Through a Retinoic Acid Response Element Embedded in Sp1 Sites", *Molecular and Cellular Biology*, 12:2976–2985 (1992).

Riaz–ul–Haq, et al., "Retinoic Acid Affects the Expression of Nuclear Retinoic Acid Receptors in Tissues of Retinol–Deficient Rats", *Biochemical and Biophysical Research Communications*, 180:1137–1144 (1991).

Riaz–ul–Haq, et al., "Differential Effects of All–Trans And 13–Cis–Retinoic Acid on mRNA Levels of Nuclear Retinoic Acid Receptors in Rat Lung and Liver", *Proc. Natl. Acad. Sci. USA*, 88:8272–8276 (1991).

Bailly et al., "Retinoic Acid Inhibits the Production of Collagenase by Human Epidermal Keratinocytes," *Chemical Abstracts* 112:48755h, p. 70 (1990).

Brinckerhoff and Harris, "Modulation by Retinoic Acid and Corticosteroids of Collagenase Production by Rabbit Synovial Fibroblasts Treated with Phorbol Myristate Acetate or Poly(Ethylene Glycol)," *Biochem. Biophys. Acta.* 677:424–432 (1981).

Drouin et al., "Glucocorticoid Receptor Binding to a Specific DNA Sequence is Required for Hormone–Dependent Repression of Pro–Opiomelanocortin Gene Transcription," *Mol. Cell Biol.* 9:5305–5314 (1989).

Haq et al., "Differential Effects of All–trans and 13–CIS–Retinoic Acid on mRNA Levels of Nuclear Retinoic Acid Receptors in Rat Lung and Liver," *Biochem. Biophys. Res. Comm.* 180:1137–1144 (1991).

Haq et al., "Retinoic Acid Affects the Expression of Nuclear Retinoic Acid Receptors in Tissues of Retinol–Deficient Rats," *Proc. Natl. Acad. Sci. USA* 88:8272–8276 (1991).

Jonat et al., "Antitumor Promotion and Antiinflammation: Down–Modulation of AP–1 (Fos/Jun) Activity by Glucocorticoid Hormone," *Cell* 62:1189–1204 (1990).

Lafyatis et al., "Interleukin–1 Stimulates and All–Trans–Retinoic Acid Inhibits Collagenase Gene Expression through its 5' Activator Protein–1–Binding Site," *Mol. Endo.* 4:973–980 (1990).

Lehman et al., "RARy2 Expression is Regulated through a Retinoic Acid Response Element Embedded in Spl Sites," *Mol. & Cell. Biol.* 12:2976–2985 (1992).

METHOD OF INHIBITING TRANSCRIPTION UTILIZING NUCLEAR RECEPTORS

This application is a continuation of U.S. Ser. No. 08/182,735, filed Jan. 14, 1994, now U.S. Pat. No. 5,643,720, which is a continuation of U.S. Ser. No. 08/032,726, filed Mar. 16, 1993, now abandoned, which is a continuation of U.S. Ser. No. 07/595,582, filed Oct. 10, 1990, now abandoned.

BACKGROUND OF THE INVENTION

References are cited throughout the specification. These references in their entirety are incorporated by reference into the specification to more fully describe the state of the art to which it pertains.

Positive and negative control of gene expression by retinoids is mediated by nuclear receptors that are part of a large family of regulatory proteins including the steroid and thyroid hormone receptors, the vitamin D receptor, and the retinoid receptors (RAR). This latter group comprises three retinoic acid (RA) receptors: RARα, β and τ, that contain highly conserved DNA and ligand binding domains. In addition a more distantly related receptor, RXR, appears to be activated by a RA metabolite.

Nuclear receptors function as transcriptional activators in the presence of their ligand. RARs, like the thyroid hormone receptors, do not require ligand binding for nuclear localization and specific DNA interaction. Until the subject invention, interaction with specific DNA sequences was thought to be essential for all regulatory functions of nuclear receptors.

Since glucocorticoids and RA are known to repress members of the collagenase family they have promise as therapeutic agents in rheumatoid arthritis where proteinases, such as collagenase and stromelysin, play an important role in joint destruction. Collagenase is the only enzyme known to cleave collagen, a major structural component of bone and cartilage destroyed by the enzyme. Retinoids inhibit the production of collagenase by synovial cells while the tumor promoter 12-0-tetradecanoylphorbol-13-acetate (TPA) and the inflammatory mediators interleukin 1 (IL1) and tumor necrosis factor alpha (TNFα) stimulate collagenase secretion and transcription.

Thus, while the RA and glucocorticoid nuclear receptors are known to repress members of the collagenase family, the mechanism of this repression was not known. A logical presumption was that the repression relates to the receptors known ability to bind DNA. However, the present invention provides the surprising discovery that these nuclear receptors actually inhibit transcription through a protein/protein interaction with AP-1, a protein complex composed of Jun homodimers and Jun/Fos heterodimers. Hence, a major discovery that regulatory function of nuclear receptors are mediated by a mechanism that does not involve direct binding to DNA is provided. This discovery provides a mechanism through which arthritis and cancer can be treated.

SUMMARY OF THE INVENTION

This invention provides a method of inhibiting the transcription of a gene, which is activated by AP-1 or an AP-1 component, comprising binding AP-1 or the component with a nuclear receptor so as to prevent the binding of AP-1 to the gene. The nuclear receptor can be the retinoic acid receptor, glucocorticoid receptor, vitamin D3 receptor, thyroid receptor, or the estrogen receptor.

Also provided is a composition of matter comprising AP-1 or an AP-1 component bound to a nuclear receptor. These methods and compositions can be used to identify and screen for new ligands of nuclear receptors useful for treatment of arthritis and cancer.

DETAILED DESCRIPTION OF THE INVENTION

The invention provides a method of inhibiting the transcription of a gene, which is activated by AP-1 or an AP-1 component, comprising binding of AP-1 or a component of it with a nuclear receptor so as to prevent the binding of AP-1 to the gene.

It is known that Jun and Fos protooncoproteins make up AP-1. Thus, in one embodiment, the AP-1 component is a Jun protein or a Fos protein or portions thereof which either individually or in combination with other components activate transcription through AP-1 responsive nucleotide sequences. Thus, by "AP-1" is meant any compound having the structure of "AP-1" necessary for the binding of AP-1 to its responsive element.

In addition, "nuclear receptor" means a receptor, such as retinoic acid receptor, glucocorticoid receptor, vitamin D3 receptor, thyroid receptor and estrogen receptor, or portions of these receptors, which retain the function of binding AP-1 or transcriptionally activating fragments of AP-1.

The retinoic acid receptor (RAR) includes RARε, RARα RARβ, RARτ and the related RXR proteins. The thyroid receptor includes erbA-T, TRα-2 and TRα-2 variant.

The gene in which transcription is inhibited can be any gene which is transcriptionally activated by AP-1 or an AP-1 component. In one embodiment, the gene encodes collagenase.

Since AP-1 is a transcriptional activator of the gene encoding collagenase, and collagenase is one of the enzymes known to break down collagen, a component of bone, the control of AP-1 mediated transcription can be utilized to treat arthritis. Likewise, since AP-1 is comprised of the protooncogene encoded products Jun and Fos, the control of AP-1 mediated transcription can be utilized to treat those cancers caused by AP-1, a Jun or Fos component or another oncogene that regualtes AP-1 activity. Examples of control of AP-1 mediated cancer include the overexpression of AP-1, the expression of mutated forms of AP-1 and the increased AP-1 activity caused by expression of oncogenes such as H-ras.

Typically, the nuclear receptor binds to its ligand, e.g. retinoic acid receptor to retinoic acid, prior to binding to AP-1 or an AP-1 component. Thus, the invention provides methods in which ligand/receptor binding is required.

However, circumstances can exist where the receptor directly binds to AP-1 or an AP-1 component.

Applicant's discovery also provides a novel composition of matter comprising AP-1 or an AP-1 component bound to a nuclear receptor. Examples of the nuclear receptor include retinoic acid, glucocorticoid, vitamin D3, thyroid and estrogen. Retinoic acid receptor includes RARε, RARα and RARτ and thyroid receptor includes erbA-T, TRα-2 and TRα-2 variant.

The invention also provides a method of promoting the transcription of a gene which is activated by AP-1 or an AP-1 component comprising preventing the binding of AP-1, or an AP-1 component, with a nuclear receptor thereby allowing AP-1 to bind the gene. Such a method, given the teaching of the subject application, could be carried out by a person skilled in the art.

The invention still further provides a method of screening a sample for ligands which bind to a nuclear receptor to form a complex which binds or interferes with AP-1 or an AP-1 component. The method comprises contacting the ligand receptor complex with AP-1 and determining the binding of the complex to AP-1, the presence of binding or interference with AP-1 activity indicating the presence of a ligand. The binding of the complex to AP-1 can result in an increased anti-cancer or anti-arthritis effect compared to a ligand known to bind a nuclear receptor. Thus, one can screen for ligands with increased specificity or affinity of the receptor/ligand complex for AP-1 or AP-1 components. These ligands can be made by standard organic synthesis and screened using the methods of the invention.

This invention provides the added discovery that there is a family of nuclear receptors, in addition to their function as DNA binding transcriptional activators, which regulate transcription through protein interactions, especially with AP-1. Thus, the invention is much more than individual receptors binding AP-1. The invention involves the discovery that the family of nuclear receptors can act as transcriptional regulators through protein/protein interactions.

EXAMPLE I

The AP-1 Site of the Collagenase Promoter is Repressed by RARs

The region of the collagenase promoter that confers repression by RA is located between residues −73 and −63, which contain the AP-1 site that is responsible for induction by TPA, TNFα and IL1 (Angel et al., Mol. Cell. Biol. 7:2256–2266 (1987a); Brenner et al., Nature 337:661–663 (1989); Lafyatis et al., Mol. Endo. 4:973 (1990)). In addition, this site confers repression by GR as shown in Example VI.

Figure 1:
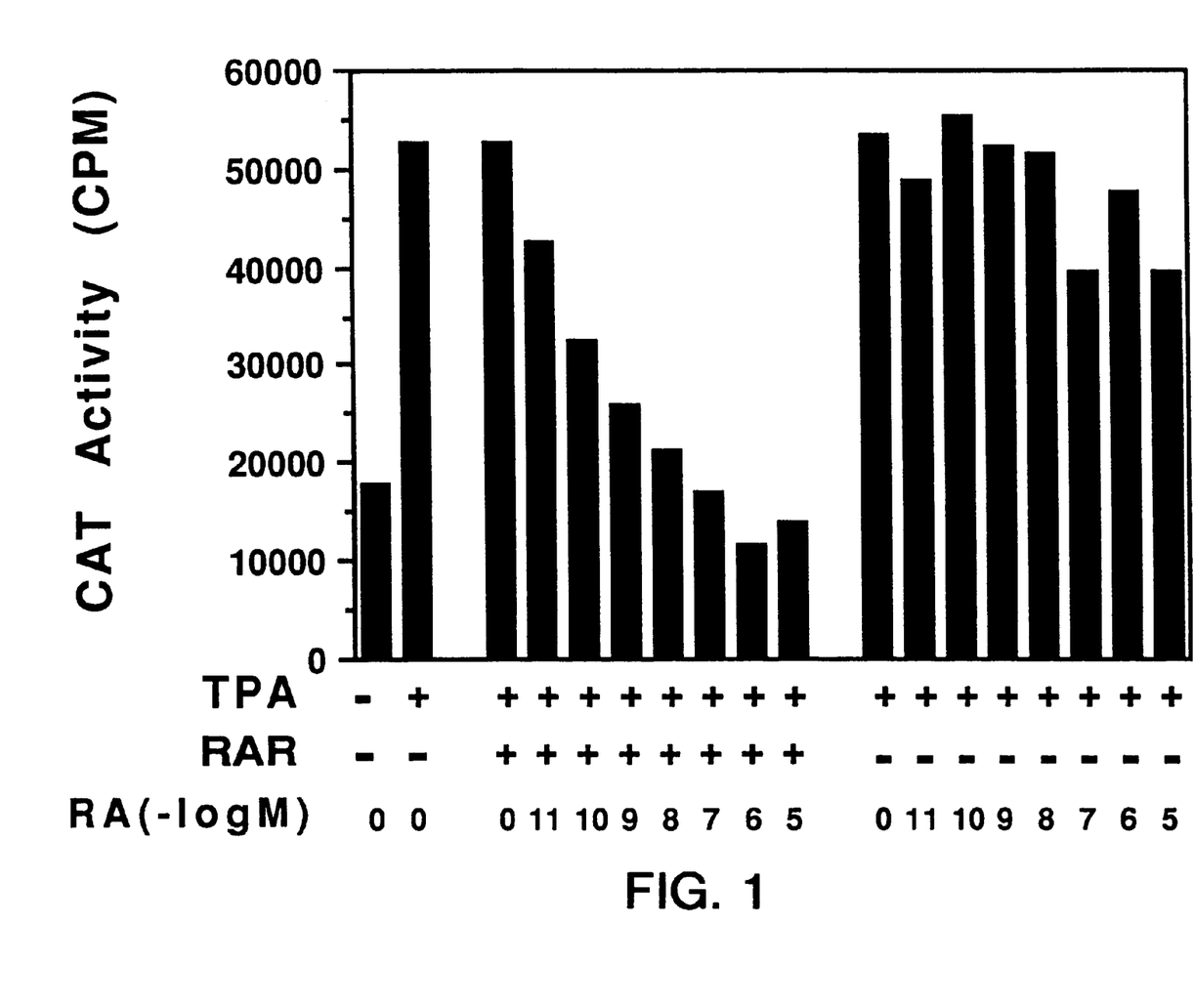
FIG. 1 shows that RARβ represses TPA induced collagenase promoter activity in a RA dependent fashion.

The −73 Col CAT reporter gene was cotransfected into HeLa with an expression vector for RARβ/ε. Cells were grown in the presence of the indicated amounts of RA and/or TPA. Repression of TPA collagenase promoter activity is observed only in the presence of RAR and is dependant on the concentration of RA.

When the −73Col-CAT construct was transfected into Hela cells, grown in the presence and absence of RA, no substantial RA-dependent decrease in its basal or TPA induced CAT activity was observed. However, when an RARβ expression vector was co-transfected with the −73Col-CAT construct, a dramatic repression of CAT activity was observed in the presence of RA, but not in the absence of RA. This repression was observed in either TPA-treated (FIG. 1) or untreated cells. Co-transfection of RARβ with the −63Col-CAT showed no effect in the presence or absence of RA. The repression of −73Col-CAT by RARβ is specific because the activity of another TPA-inducible promoter, that of cFos was not affected. Exchanging the RARβ expression vector for the RARτ vector yielded similar results. The repression of the TPA induced activity of −73 Col-CAT by RARβ is concentration dependent: half maximal inhibition occurred at $10^{-9}$ M RA, while maximal repression required $10^{-6}$ M RA (FIG. 1). A similar concentration dependence was found for activation of an RARε reporter gene by RARβ. Thus, the repression of collagenase transcription by RA is mediated by the AP-1 site and dependent on the level of RA activated RAR. This implies that the RARs either function by direct interaction with the AP-1 site and thereby interfere with AP-1 binding through a competitive mechanism, or alternatively by a mechanism that does not require direct binding of the RAR to the AP-1 site, but involves RAR-mediated interference with AP-1 activity. Despite a previous report that RA may repress collagenase expression by inhibition of cFos induction (Lafyatis et al., 1990 supra), we have not been able to find any effect of RA and RARs on the cFos promoter, in either HeLa (FIG. 1) or F9 cells.

To further demonstrate the involvement of AP-1 in repression of collagenase transcription by RA, we transfected the −73 Col-CAT reporter into F9 cells which have very low endogenous AP-1 activity. Co-transfection of −73 Col-CAT with a cJun expression vector activates its transcription, while a cFos expression vector does not lead to significant activation. As previously shown (Chiu et al., Cell 54:541–552 (1988)) co-transfection with a combination of cJun and cFos expression vector leads to further activation of −73 Col-CAT expression. In either case, expression of −73 Col-CAT was inhibited by RA, and further inhibition was observed in the presence of co-transfected RARβ expression vector. Thus, elevating the level of RAR expression in F9 cells increases the repression of AP-1 activity by RA. Inhibition occurs regardless whether AP-1 activity is due to cJun homodimers or cJun/cFos heterodimers.

EXAMPLE II

Jun and Fos Repress RAR Activity

Next, we investigated whether the functional antagonism between RAR and AP-1 activity is limited to the AP-1 target site or whether it can be extended to targets which are positively regulated by RARs.

Figure 2:
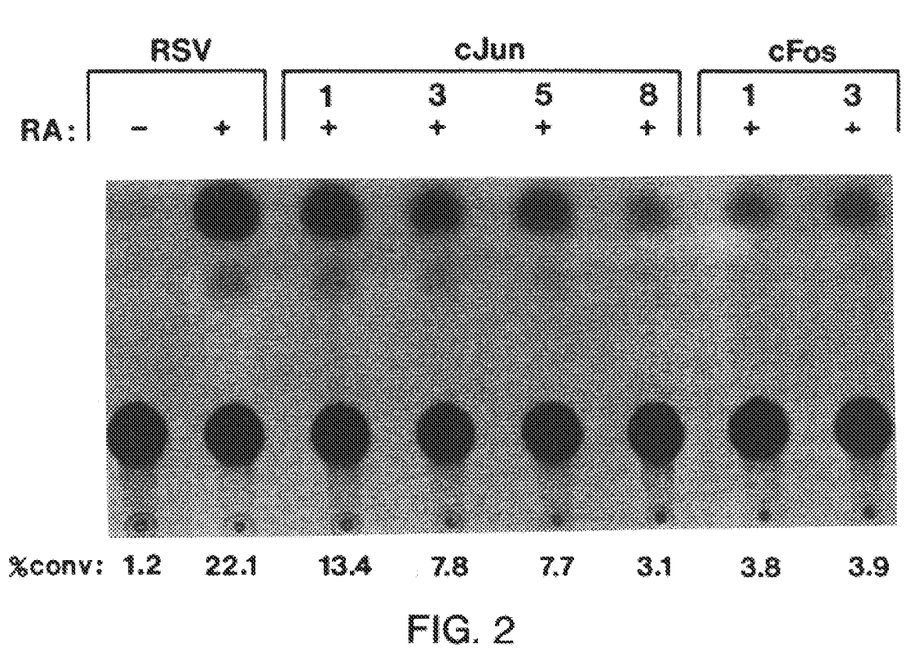
FIG. 2 shows inhibition of RAR activity by cJun and cFos.

F9 cells were transfected with the RA responsive reporter T3RE$_2$-CAT (2 μg) in the presence of 8 μg of an empty expression vector (RSV) or the indicated amounts (in μg) of cJun or cFos expression vectors. After transfection, the cells were incubated in the absence or presence of $10^{-7}$ M RA for 24 hours before harvesting and determination of CAT activity. The T3RE$_2$-CAT reporter was co-transfected into F9 cells with 1 μg of either a mutant cJun (cJM), cJun, cFos or a combination of cJun and cFos expression vectors. RA treatment was done as indicated above.

Co-transfection of the reporter T3RE$_2$-CAT that contains two RAR responsive elements in front of the HSV-TK promoter (Glass et al., Cell 54:313–323 (1988)), with increasing concentrations of either a cJun or a cFos expression vector, resulted in strong dose-dependent inhibition of its activation by RA (FIG. 2). Similar inhibition has also been obtained when a CAT reporter gene containing the RARE derived from the RARβ promoter was used. Co-transfection of T3RE$_2$-CAT with cFos expression vector resulted in a more effective inhibition of its induction than a co-transfection with a cJun expression vector. No further inhibition was obtained by co-transfection with a combination of the cJun and cFos expression vectors. Hence, elevated levels of both AP-1 constituents can repress the activation of an RARE by RAR.

EXAMPLE III

RAR Does Not Bind the AP-1 Site, But Inhibits Jun DNA Binding

Recently, it was reported that AP-1 may repress osteocalcin induction by RA and vitamin D by binding to a site embedded within an RA and vitamin D response element (Schüle et al., 1990a). We therefore investigated the possibility that RAR can bind specifically to the AP-1 site or neighboring sequences of the collagenase promoter.

Figure 3:
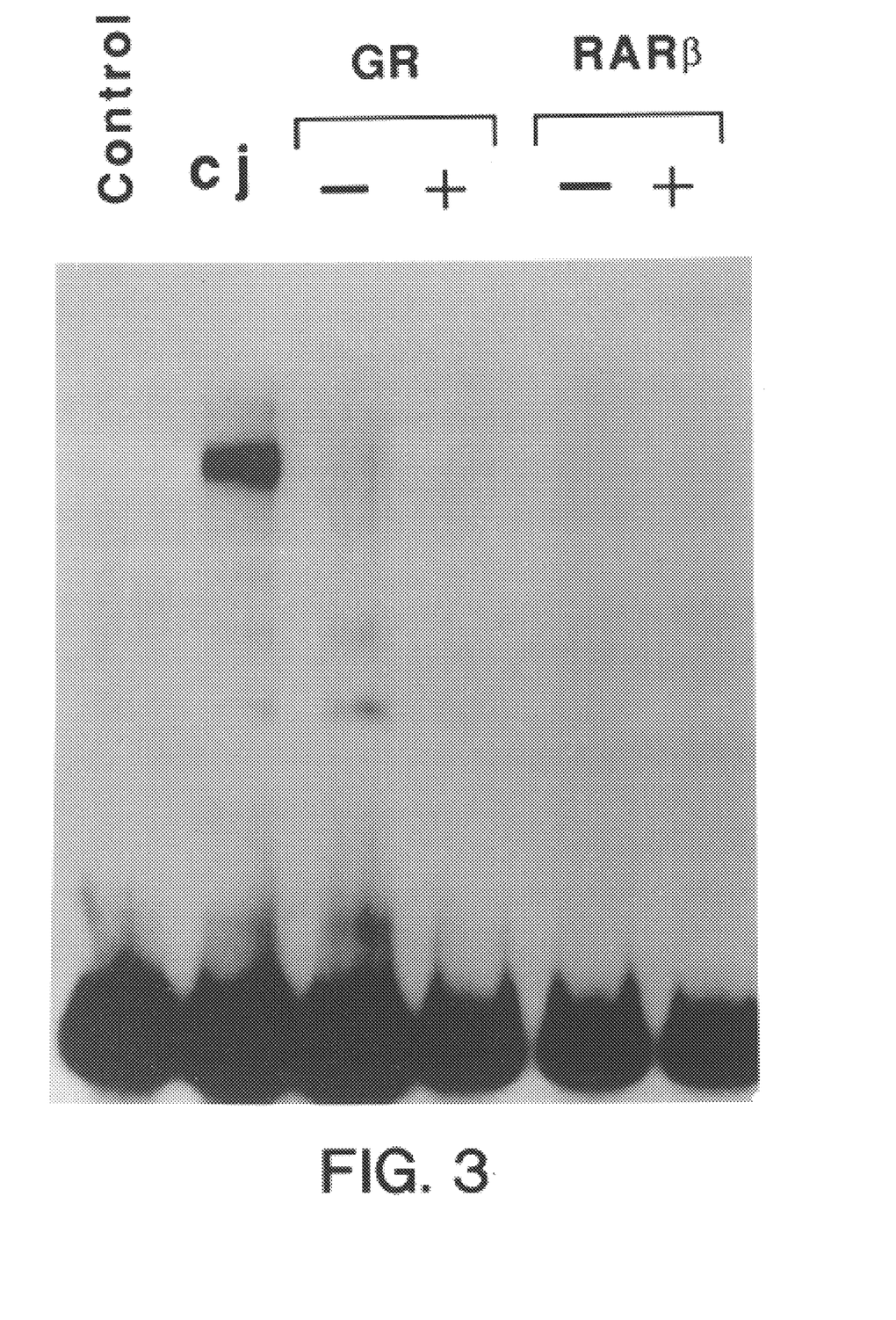
FIG. 3 shows that RARB does not bind to the collagenase promoter.

In vitro synthesized glucocorticoid receptor (GR) and retinoic acid receptor (RAR) were incubated with $^{32}$P-labelled DNA fragment derived from −73 COL-CAT by Hind III and Bam HI digestion. Protein-DNA complex was analyzed by gel retardation assay. Control represents the binding of unprogrammed reticulocyte lysate.

Gel retardation experiments were carried out with a 60 bp DNA fragment containing the collagenase AP-1 site. While specific binding of cJun to this site (FIG. 3) or a synthetic AP-1 site was readily detected, RARβ did not bind to either site (FIG. 3). As reported in Example VI, GR also did not bind to either probe (FIG. 3). Thus, the binding of RAR to site overlapping the AP-1 site cannot account for repression of collagenase induction, neither does the AP-1 site constitute a minimal RAR recognition element as previously suggested (Schüle et al., supra).

As an explanation for its ability to repress AP-1 activity, we examined the effect of RAR on AP-1 binding activity.

In vitro synthesized cJun protein was incubated with one-fold (1) or five-fold (5) excess of in vitro synthesized RARβ or RARτ protein at 37° C. for 15 minutes. The effect of RARβ or RARτ or cJun binding was analyzed by gel retardation assay. As control the inhibition effect of GR on cJun binding is shown in FIG. 4.

Figure 4:
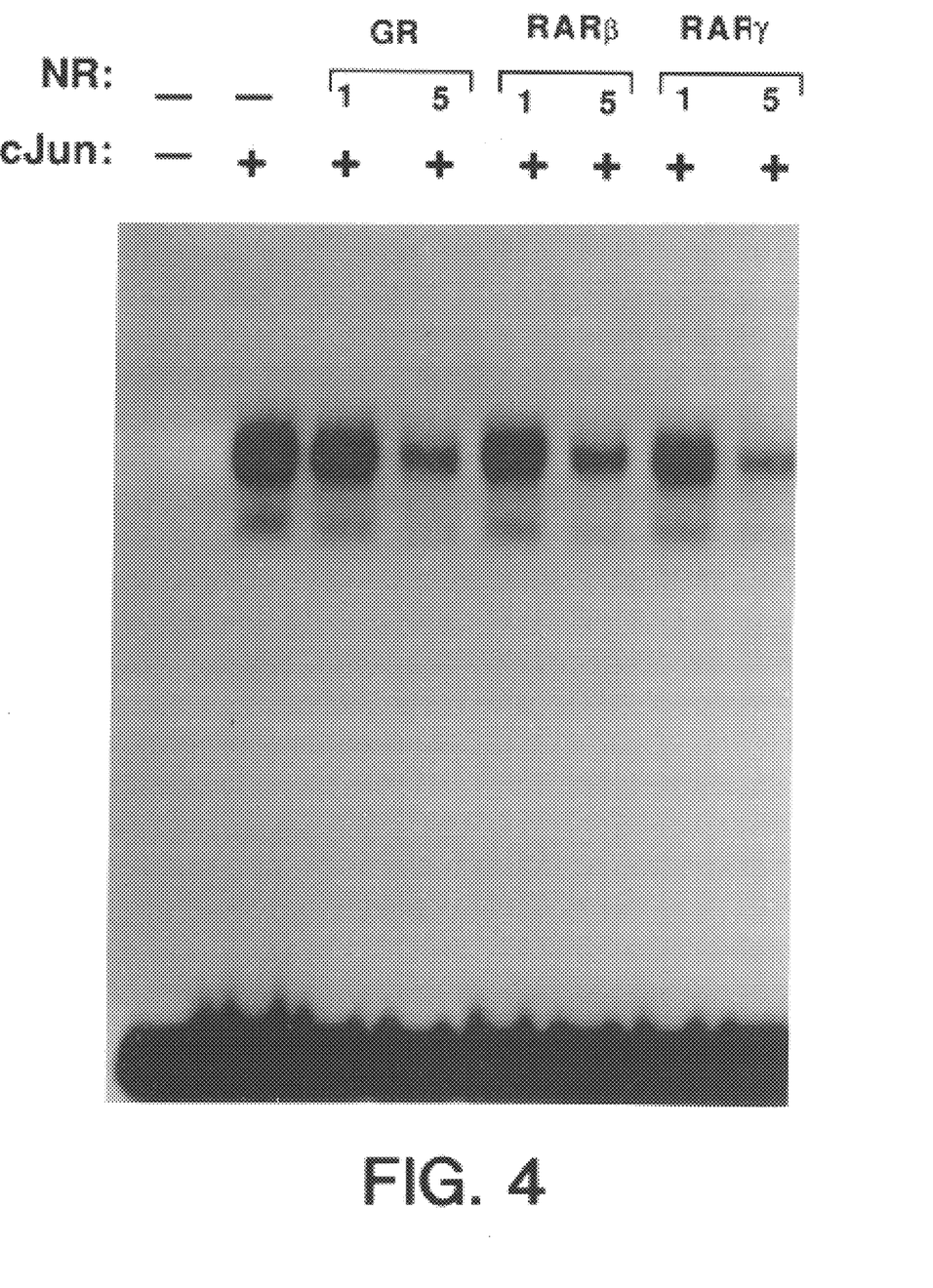
FIG. 4 shows inhibition of cJun binding by RARβ and RARτ on synthetic AP-1 site.

When cell-free translated RARβ or RARτ proteins were mixed with bacterially produced or in vitro translated cJun, a significant inhibition of cJun binding to the AP-1 site was seen (FIG. 4). The Inhibition of cJun binding to the AP-1 site was dependent on the amount of RARs used, and was also observed in response to pre-incubation with in vitro synthesized GR (FIG. 4). As shown for the GRs in Example VI, this in vitro inhibition of cJun binding was ligand independent. The inhibition of Jun binding activity is a specific effect of each receptor because pre-incubation of the cell-free translated RARβ with anti-RAR antibodies prevented this inhibition, while pre-incubation with anti-GR or preimmune serum had no effect. Likewise, the inhibitory activity of cell-free translated GR is inhibited by anti-GR antibodies, but not by anti-RAR or preimmune serum. Because of its increased stability, the cJun/cFos heterodimer exhibits stronger AP-1 binding activity than the cJun homodimer. We therefore investigated whether the binding of the heterodimers could also be inhibited by the RAR. DNA binding was strongly enhanced by the addition of in vitro synthesized cFos, while cFos by itself did not bind the AP-1 site. Addition of RAR resulted in a comparable degree of repression for both cJun and cJun/cFos binding to the AP-1 site.

EXAMPLE IV

Jun Inhibits RAR DNA Binding

The inhibition of cJun or cJun/cFos DNA binding by RAR results from an interaction between the two classes of proteins in which the DNA binding activities of both proteins are impaired. Additionally, AP-1 could interfere with RAR function by competing for RARE binding. We therefore also investigated whether cJun could bind to the RARE and/or inhibit RAR DNA binding.

In vitro synthesized RAR protein was incubated with $^{32}$P-labelled DNA fragment containing one copy of RARE. The binding of RAR on RARE was analyzed by gel retardation assay. In competition experiments, 50-fold excess of unlabelled RARE (S) or comparable length of non-specific oligonucleotides (N) were included in the binding reaction. C represents the binding of unprogrammed reticulocyte lysate in FIG. 5. To test the effect of cJun protein on RAR binding, excess amount of bacterial expressed Jun protein was incubated with RAR at 37° C. for 15 minutes before the addition of DNA. When anti-cJun (a cJun) was used, it was incubated with Jun protein at room temperature for 45 minutes before mixing with RAR protein.

Figure 5:
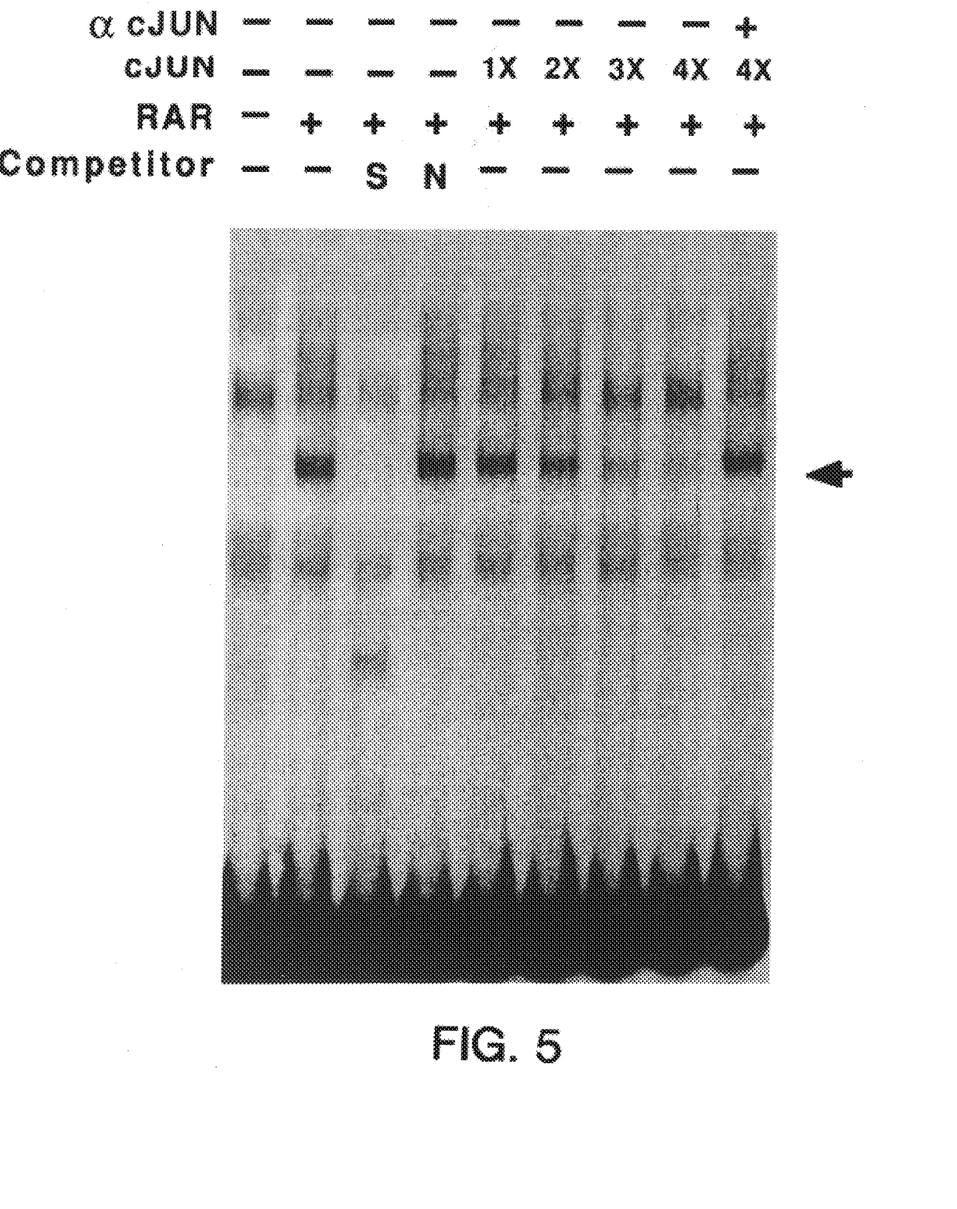
FIG. 5 shows inhibition of RAR binding to RARε by cJun protein.

Specific binding of RARβ to the synthetic RARE derived from the RARβ promoter region is shown in FIG. 5. When bacterially produced cJun protein was pre-incubated with RARβ, it inhibited its DNA binding activity in a concentration dependent manner. However, cJun did not increase the retention of the labelled RARE or lead to appearance of new protein-DNA complexes (FIG. 5). This inhibition was specific as it was prevented by pre-incubation of cJun with anti-Jun antibodies.

EXAMPLE V

Thyroid Hormone Receptor Represses Collagenase Promoter Activity

Figure 6:
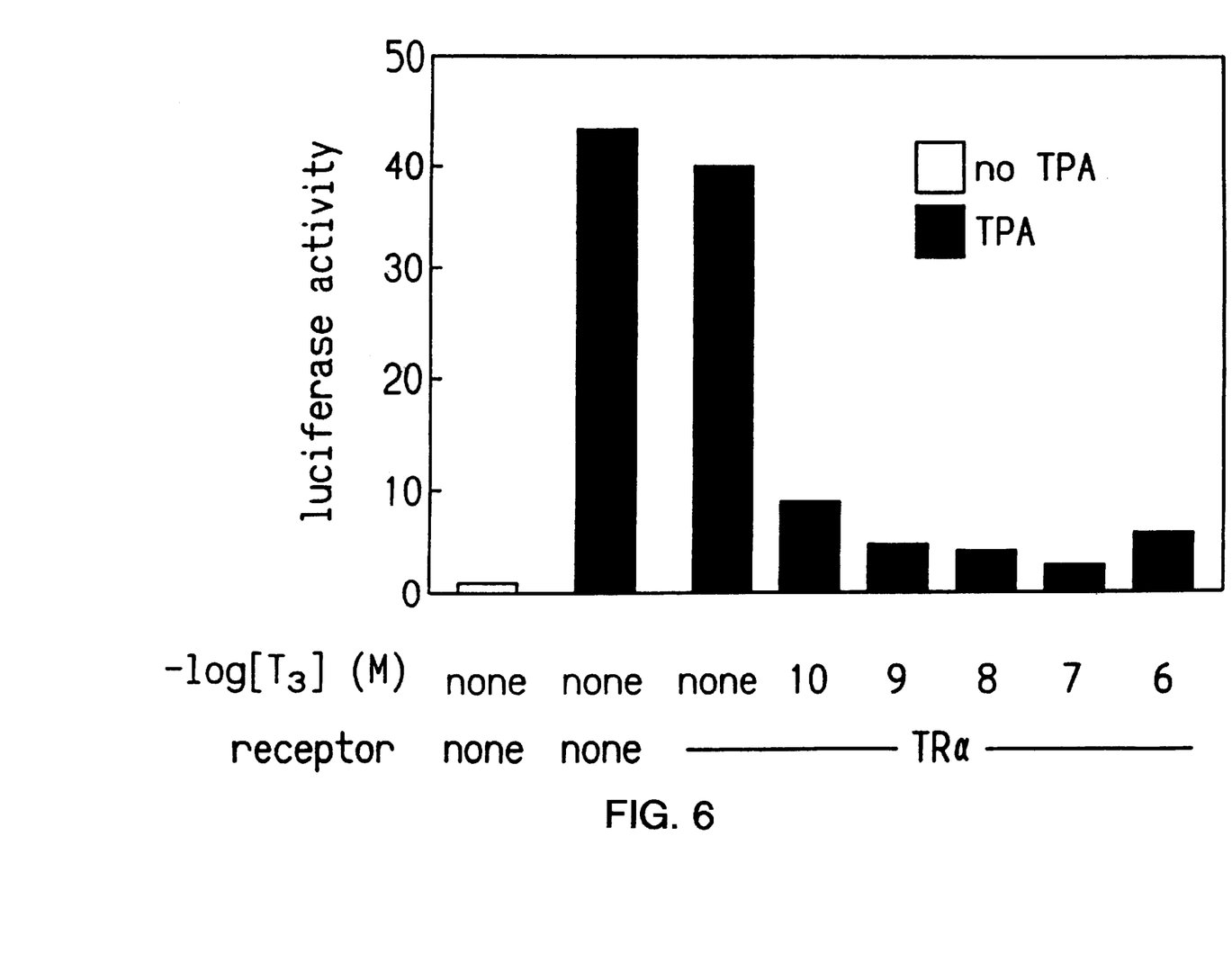
FIG. 6 shows that TRα represses TPA induced collagenase promoter activity in a T3 dependent fashion.

In addition, applicants have discovered that the thyroid hormone receptor, in the presence of Thyroid hormone, binds AP-1 through a protein/protein interaction and inhibits the transcription of AP-1 activated genes. Specifically, TRα represses TPA induced collagenase promoter activity in a T3 dependent fashion. The −73 Col CAT reporter gene was cotransfected into CV-1 cells with an expression vector for RARβ/ε. Cells were grown in the presence of the indicated amounts of T3 and/or TPA. Repression of TPA collagenase promoter activity is dependant on the concentration of T3. These results are shown in FIG. 6.

EXAMPLE VI

Glucocorticoid Receptor Inhibits AP-1 Activity

Applicants have also shown that the glucocorticoid receptor (GCR) is a potent inhibitor of AP-1 activity (Jun/Fos) and both c-Jun and c-Fos are potent repressors of GCR activity. In vitro experiments using purified GCR and c-Jun proteins showed that mutual repression is due to direct interaction between the two. Direct interaction between GCR and either c-Jun or c-Fos is demonstrated by cross-linking and coimmunoprecipitation. These findings also revealed a cross talk between two major signal transduction systems used to control gene transcription in response to extracellular stimuli, and a novel protein/protein interaction between the GCR and AP-1. The data demonstrating these findings is set forth in Yang-Yen et al., Cell 62:1205–1215, (1990).

Although the invention has been described with reference to the presently preferred embodiment, it should be understood that various modifications can be made without departing from the spirit of the invention. Accordingly, the invention is limited only by the following claims.

What is claimed is:

1. A method of inhibiting the transcription of a gene, which is activated by AP-1 or an AP-1 component, comprising binding AP-1 or the component with a nuclear receptor so as to prevent the binding of AP-1 to the gene, wherein transcription is inhibited.

2. The method of claim 1, wherein the AP-1 component is a Jun protein.

3. The method of claim 1, wherein the nuclear receptor is a glucocorticoid receptor.

4. The method of claim 1, wherein the nuclear receptor is a vitamin D3 receptor.

5. The method of claim 1, wherein the nuclear receptor is an estrogen receptor.

6. The method of claim 1, wherein the gene is the gene encoding collagenase.

7. The method of claim 1, wherein the receptor is bound to its ligand.

8. The method of claim 1, wherein the nuclear receptor is a retinoic acid receptor.

9. The method of claim 8, wherein the retinoic acid receptor is selected from the group consisting of RARϵ, RARα RARβ, RARτ, and RXR.

10. The method of claim 1, wherein the nuclear receptor is a thyroid receptor.

11. The method of claim 10, wherein the thyroid receptor is selected from the group consisting of erbA-T and TRα-2.

12. A method of inhibiting the transcription of a gene which is activated by a nuclear receptor which binds AP-1 or an AP-1 component comprising binding the receptor with AP-1 or an AP-1 component so as to prevent the binding of the nuclear receptor to the gene, wherein transcription is inhibited.

13. A composition of matter comprising AP-1 or an AP-1 component bound to a nuclear receptor.

14. The composition of claim 13, wherein the AP-1 component is selected from the group consisting of a Jun and a Fos protein.

15. The composition of claim 13, wherein the nuclear receptor is a glucocorticoid receptor.

16. The composition of claim 13, wherein the nuclear receptor is a vitamin D3 receptor.

17. The composition of claim 13, wherein the nuclear receptor is an estrogen receptor.

18. The composition of claim 13, wherein the nuclear receptor is a retinoic acid receptor.

19. The composition of claim 18 wherein the retinoic acid receptor is selected from the group consisting of RARϵ, RARα, RARβ and RARτ and RXR.

20. The composition of claim 13, wherein the nuclear receptor is a thyroid receptor.

21. The composition of claim 20, wherein the thyroid receptor is selected from the group consisting of erbA-T and TRα-2.

22. A method of promoting the transcription of a gene which is activated by AP-1 or an AP-1 component, comprising preventing the binding of AP-1 or an AP-1 component with a nuclear receptor thereby allowing AP-1 to bind the gene, wherein transcription is promoted.

* * * * *